United States Patent [19]

Kondo et al.

[11] Patent Number: 4,481,187

[45] Date of Patent: Nov. 6, 1984

[54] CLEAR LIQUID SKIN COSMETIC COMPOSITIONS

[75] Inventors: Mitsuo Kondo; Hiromi Minamino; Yasuhisa Otani, all of Odawara; Akira Miyashita, Yokohama; Kenzo Okada, Tokyo; Takashi Kuramoto, Onomichi, all of Japan

[73] Assignees: Kanebo, Ltd.; Maruzen Kasei Co., Ltd., both of Japan

[21] Appl. No.: 462,720

[22] Filed: Feb. 1, 1983

Related U.S. Application Data

[63] Continuation-in-part of Ser. No. 241,524, Mar. 9, 1981, abandoned.

[30] Foreign Application Priority Data

Mar. 8, 1980 [JP] Japan ................................. 55-29608
Oct. 2, 1980 [JP] Japan ............................... 55-138512

[51] Int. Cl.$^3$ ..................... A61K 7/021; A61K 7/15; A61K 7/46; A61K 7/48
[52] U.S. Cl. ................................. 424/63; 252/522 R; 424/73; 424/358; 424/365; 536/18.1
[58] Field of Search ..................... 424/73, 63; 536/4; 252/522 R, 522

[56] References Cited

U.S. PATENT DOCUMENTS 4,278,657  7/1981  Tezuka et al. ..................... 424/63

FOREIGN PATENT DOCUMENTS 1157604  11/1963  Fed. Rep. of Germany .......... 536/4
1301851   7/1962  France .................................. 536/4
41-16398  9/1966  Japan .................................... 536/4

OTHER PUBLICATIONS

Martindale, 26th Ed., 1972, The Extra Pharmacopoeia, pp. 563, 714, 715.
Beaton et al., 1955, J. Chem. Soc., (London), Part 3, pp. 3126-3129.

*Primary Examiner*—Dale R. Ore
*Attorney, Agent, or Firm*—McGlew and Tuttle

[57] ABSTRACT

Disclosed is a clear liquid skin cosmetic composition (e.g., a lotion) in which one or more oily substances (such as oil-soluble perfumes, hormones and the like) are solubilized in water with the aid of a solubilizing agent comprising an 18α-glycyrrhizin (18α-glycyrrhizic acid sodium salt, potassium salt or ammonium salt) that is a novel compound derived from a conventional glycyrrhizin (i.e., any form of 18β-glycyrrhizin extracted from licorice root) or a glycyrrhizin composition consisting of an 18α-glycyrrhizin and an 18β-glycyrrhizin. This skin cosmetic composition is not irritative to the skin as contrasted with skin cosmetic compositions prepared by using a synthetic surface-active agent as the solubilizing agent, and is not subject to gelation in a slightly acidic to acidic pH range as contrasted with skin cosmetic compositions prepared by using an 18β-glycyrrhizin alone as the solubilizing agent. Moreover, this skin cosmetic composition exerts a mild action on the skin without causing irritation thereto, gives an agreeable feeling, and has excellent fluidity, usability and storage stability.

10 Claims, No Drawings

CLEAR LIQUID SKIN COSMETIC COMPOSITIONS

This is a continuation-in-part of application Ser. No. 241,524 filed Mar. 9, 1981 now abandoned.

BACKGROUND OF THE INVENTION

(1) Field of the Invention

This invention relates to clear liquid skin cosmetic compositions which contain a solubilizing agent comprising an 18α-glycyrrhizin (18α-glycyrrhizic acid sodium salt, potassium salt or ammonium salt) that is a novel compound obtained by isomerization of a conventional glycyrrhizin (i.e., any form of 18β-glycyrrhizin extracted from licorice root) or a glycyrrhizin composition consisting of an 18α-glycyrrhizin and an 18β-glycyrrhizin. More particularly, it relates to such clear liquid skin cosmetic compositions in which the difficulties inherent in the use of a solubilizing agent comprising a conventional glycyrrhizin (18β-glycyrrhizin) alone or a synthetic surface-active agent are overcome.

(2) Description of the Prior Art

It is well known that aqueous solutions of conventional glycyrrhizins (18β-glycyrrhizic acid sodium salt, potassium salt and ammonium salt) present peculiar phenomena. That is, they form a gel and show a reduction in solubility in the pH range of from 2.5 to 6.

A skin cosmetic of the gel type has been developed by utilizing the above-described gelation phenomenon of conventional glycyrrhizins (Japanese Patent Publication No. 21397/1970). However, this skin cosmetic involves a number of difficulties: (1) The gel is lacking in fluidity and scarcely adherent to the fingers, so that it is hard to take out of the container (e.g., the bottle). (2) When applied to the skin, the gel can hardly be destroyed (or liquefied) by pressing it with fingers or palms and, moreover, can hardly be spread evenly because it tends to slip on the skin. (3) The gel undergoes syneresis (i.e., the separation of water) during longterm storage, which impairs its stability and appearance to a marked degree. (4) The bubbles which are formed during the blending step are hard to remove and hence remain in the gel. These difficulties hinder the aforesaid skin cosmetic from being put to practical use.

In addition, Japanese Patent Laid-Open No. 151736/1977 discloses a hormone-blended lotion which is prepared by solubilizing a hormone (such as diethylstilbestrol, estradiol or the like) in an aqueous solution of ethyl alcohol with the aid of a conventional glycyrrhizin (i.e., 18β-glycyrrhizic acid dipotassium salt) and adjusting the pH of the resulting clear solution to 6.1 or greater. However, since the capacity of the conventional glycyrrhizin for solubilizing oily substances (such as hormones and the like) is rather limited, the product tends to become turbid after it has been stored under severe temperature conditions for a long period of time. Moreover, the time required to defoam the product is relatively long because the foam which is formed in an aqueous solution of the conventional glycyrrhizin disappears slowly.

Recently, the so-called acidic skin cosmetics which are adjusted to pH values approximating the pH(4.0–6.0) of the skin and considered to exert a mild action on the skin have come into common use.

However, conventional glycyrrhizins induce a marked degree of gelation and a reduction in solubility in the pH range of from 2.5 to 6 and, in particular, from 3.0 to 5.5. Accordingly, they are utterly useless in the preparation of acidic liquid skin cosmetics which have excellent properties (such as clarity, fluidity, feeling, solubilization stability and the like) and are easy to use. Moreover, the aforesaid gelation and the ensuing sharp rise in viscosity make it difficult to defoam the product. For these reasons, conventional glycyrrhizins have been applicable only to certain types of lotions, for example, the hormone-blended lotion (with a pH value of 6.1 or greater) disclosed in Japanese Patent Laid-Open No. 151376/1977.

In order to overcome the above-described difficulties, the present inventors have performed intensive and extensive studies and have discovered that, if an 18α-glycyrrhizin (novel compound) of the structural formula (1) which will be given later or a glycyrrhizin composition consisting of such an 18α-glycyrrhizin and an 18β-glycyrrhizin (conventional glycyrrhizin) of the structural formula (2) which will be given later is used as a solubilizing agent for oily substances, clear liquid skin cosmetic compositions having excellent properties under any desired pH conditions can be readily and advantageously prepared on an industrial scale. The present invention is based on this discovery.

SUMMARY OF THE INVENTION

It is an object of the present invention to provide a clear liquid skin cosmetic composition which exerts a mild action on the skin without causing irritation thereto, gives an agreeable feeling, has excellent fluidity, usability and storage stability, and presents a clear and attractive appearance.

It is another object of the present invention to provide novel solubilizing agents.

It is still another object of the present invention to provide a clear liquid cosmetic composition which permits easy design of its formulation, can be readily prepared on an industrial scale, and does not use any synthetic surface-active agents (or any synthetic solubilizing agents).

The above and other objects of the invention are accomplished by a clear liquid skin cosmetic composition which consists essentially of a solubilizing agent, an oily substance and water, the solubilizing agent comprising at least one 18α-glycyrrhizin of the structural formula

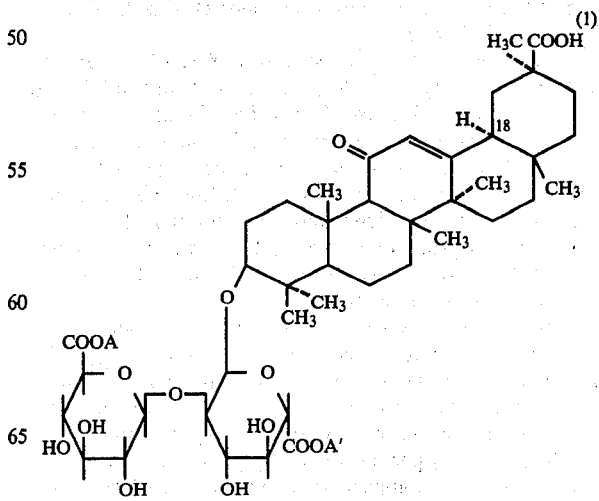

(1)

where A and A' independently represent sodium atoms, potassium atoms or ammonium groups, or a glycyrrhizin composition consisting of from 30 to 98 mole % of an 18α-glycyrrhizin as defined above and from 2 to 70 mole % of an 18β-glycyrrhizin of the structural formula

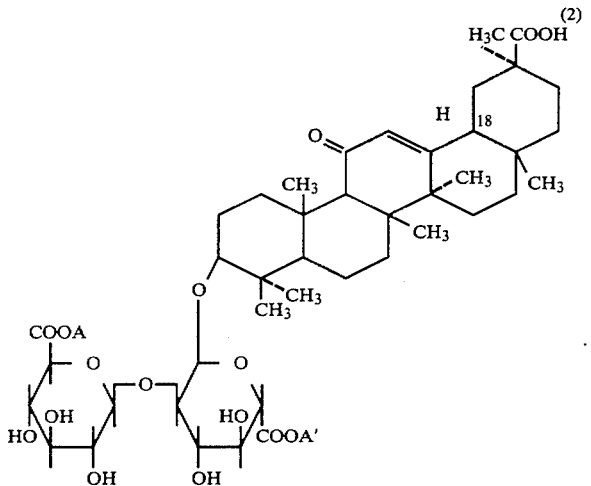

where A and A' independently represent sodium atoms, potassium atoms or ammonium groups.

DETAILED DESCRIPTION OF THE PREFERRED EMBODIMENTS

The 18α-glycyrrhizins which are within the scope of the structural formula (1) given above and can be used in the practice of the present invention are novel compounds and disclosed in Japanese Patent Application No. 24023/1980 filed Feb. 29, 1980. Similarly, the glycyrrhizin compositions which consist of from 30 to 98 mole % of an 18α-glycyrrhizin as described above and from 2 to 70 mole % of an 18β-glycyrrhizin within the scope of the structural formula (2) given above and can be used in the practice of the present invention are novel compositions and disclosed in Japanese Patent Application No. 580/1980 filed Jan. 9, 1980. These compounds and compositions were invented by Akira MIYASHITA, Kenzo OKADA and Takashi KURAMOTO who are among the present inventors, and applications for patent on these inventions have been filed in Japan (as described above), U.S.A., Great Britain and France.

As can be seen from the structural formula (1) given above, the aforesaid 18α-glycyrrhizins are different from conventional glycyrrhizins (i.e., the glycyrrhizins within the scope of the structural formula (2) only in that the hydrogen atom located at the 18-position has the α-configuration. (In order to distinguish between these novel glycyrrhizins and conventional glycyrrhizins extracted from licorice root, the former compounds are herein referred to as 18α-glycyrrhizins and the latter ones as 18β-glycyrrhizins.)

While 18α-glycyrrhizins have some properties in common with 18β-glycyrrhizins, they also show such peculiar properties as cannot be expected from the slight structural difference consisting in the distinct steric configuration of only one hydrogen atom.

The main properties of 18α-glycyrrhizins are described below in comparison with those of 18β-glycyrrhizins. All of the 18α-glycyrrhizin samples appearing in the following description are those prepared in the examples which will be given later.

(a) Melting point (decomposition point)

Glycyrrhizins show no melting point. The decomposition points of typical 18α- and 18β-glycyrrhizins are as follows:

| Sample | 18α-Isomer | 18β-Isomer |
|---|---|---|
| Free acid | 206° C. | 210° C. |
| Monoammonium salt | 212–213° C. | 216° C. |
| Monopotassium salt | 248° C. | 246° C. |

(b) Specific optical rotation $[\alpha]_D^{20}$ (as measured with a 1% (w/v) solution in 50% (v/v) ethanol)

| Sample | 18α-Isomer | 18β-Isomer |
|---|---|---|
| Free acid | +26.1° | 60.4° |
| Monoammonium salt | +23.2° | 57.1° |
| Monopotassium salt | +23.0° | 56.0° |

(c) Ultraviolet absorption spectrum

Measurements were made of the ultraviolet absorption spectra of 18α- and 18β-glycyrrhizic acid monoammonium salt dissolved in 50% (v/v) ethanol. The values for $\lambda_{max}$, $E_{1\ cm}^{1\%}$ and $\epsilon$ are as follows:

|  | 18α-Isomer | 18β-Isomer |
|---|---|---|
| $\lambda_{max}$ | 246 nm | 251 nm |
| $E_{1\ cm}^{1\%}$ | 128.7 | 136.0 |
| $\epsilon$ | 10,810 | 11,420 |

(d) Infrared absorption spectrum

The results obtained with KBr tablets indicate that there is no appreciable difference between an 18α-isomer and its corresponding 18β-isomer.

(e) Solubility

Monopotassium, monosodium, monoammonium, disodium, dipotassium and diammonium salts are easily soluble in water and sparingly soluble in methanol and ethanol. (The solubility and dissolution rate of an 18α-isomer are both superior to those of its corresponding 18β-isomer.)

(f) Solution properties

The solution properties of 18α-isomers are significantly different in many respects from those of 18β-isomers, as described below in detail.

(i) Aqueous solution of 18α-isomers are stable even in the acidic pH range where 18β-isomers would induce gelation. This can be seen in Table 1 showing the viscosities of an aqueous solution of monosodium salt at various pH values. Similar differences can be recognized with regard to other salts than monosodium salt.

TABLE 1

| Sample Concentration | | 18α-Isomer | | 18β-Isomer | |
|---|---|---|---|---|---|
| | | 0.5% | 2.0% | 0.5% | 2.0% |
| pH | 6.0 | 1.06 | 1.07 | 1.07 | 1.20 |
| | 5.5 | 1.07 | 1.10 | 1.07 | >30 |
| | 5.0 | 1.07 | 1.07 | 2.03 | >30 |

TABLE 1-continued

| Sample | 18α-Isomer | | 18β-Isomer | |
|---|---|---|---|---|
| Concentration | 0.5% | 2.0% | 0.5% | 2.0% |
| 4.5 | 1.05 | 1.10 | >30 | >30 |
| 4.0 | 1.03 | 1.03 | >30 | >30 |

Note: The pH values of the test solutions were adjusted with 1N NaOH or 1N HCl. Their viscosities were measured at 20° C. with an Ubbelohde viscometer and expressed in centipoises (cps).

(ii) Aqueous solutions of an 18α- and an 18β-isomer are placed in test tubes, foamed by shaking the test tubes under the same conditions, and allowed to stand. Then, as can be seen from the data of Table 2, the aqueous solution of the 18α-isomer shows a much higher rate of foam disappearance than that of the 18β-isomer does. (However, there is no appreciable difference in foaming properties.)

TABLE 2

| Time elapsed | Rate of foam disappearance (%) | |
|---|---|---|
| (minutes) | 18α-Isomer | 18β-Isomer |
| 10 | 46.0 | 20.0 |
| 30 | 82.1 | 25.1 |
| 60 | 88.5 | 26.5 |
| 90 | 91.0 | 28.7 |

Note: The test solutions were 0.5% aqueous solutions of 18α- and 18β-glycyrrhizic acid monopotassium salt. The rate of foam disappearance was calculated from the height of the foam.

The aforesaid 18α-glycyrrhizins can be prepared in the following manner: Any form of 18β-glycyrrhizin extracted from licorice root is dissolved in water or alcohol and heated in the presence of alkali to convert the 18β-glycyrrhizin into an 18α-glycyrrhizic acid salt. Then, 18α-glycyrrhizic acid can be obtained by isolating the resulting 18β-glycyrrhizic acid salt from the reaction mixture in the form of free acid. Subsequently, the free acid thus obtained may be converted into a salt as desired.

The chemical structure of 18α-glycyrrhizins can be confirmed in the following manner:

(1) Elemental analysis provides substantially the same values as calculated on the assumption that 18α-glycyrrhizins are isomeric with 18β-glycyrrhizins. Some examples of analytical data are given below.

| | Calculated | Found |
|---|---|---|
| | (i) Fee acid | |
| C | 61.30% | 61.10% |
| H | 7.59% | 7.62% |
| | (ii) Monoammonium salt | |
| C | 60.01% | 60.32% |
| H | 7.80% | 7.70% |
| N | 1.67% | 1.61% |

(2) Hydrolysis of an 18α-glycyrrhizin with 10% sulfuric acid produces glycyrrhetinic acid in which the hydrogen atom located at the 18-position has the α-configuration (hereinafter referred to as 18α-glycyrrhetinic acid) and glucuronic acid. Similarly, hydrolysis of an 18β-glycyrrhizin produces glycyrrhetinic acid in which the hydrogen atom located at the 18-position has the β-configuration (hereinafter referred to as 18β-glycyrrhetinic acid) and glucuronic acid. Thus, the hydrolysis product of an 18α-glycyrrhizin differs from that of an 18β-glycyrrhizin only in the steric configuration of the hydrogen atom located at 18-position of the glycyrrhetinic acid. (It is to be understood that 18α-glycyrrhetinic acid is a well-known compound and can be identified by comparison with an authentic sample.)

(3) The molar ratio of glucuronic acid to 18α-glycyrrhetinic acid present in the aforesaid hydrolysis product of an 18α-glycyrrhizin is 2:1. (In addition, the acid hydrolysis product of 18β-glycyrrhizic acid has been analyzed. The molar ratio of glucuronic acid to 18β-glycyrrhetinic acid present therein is also 2:1, which agrees with the theoretical value.)

(4) When subjected to a chemical process comprising methylation with methyl iodide, reduction with LiAlH₄, remethylation and methanolysis, an 18α-glycyrrhizin produces only two methylated sugars of the structural formulas

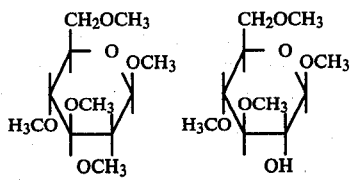

This result agrees with that obtained by subjecting an 18β-glycyrrhizin to the same chemical process.

The above-described analytical results indicate that both the aglycone moiety and the glucuronic moiety of the novel compound obtained by treating an 18β-glycyrrhizin with alkali are in no way different from those of the 18β-glycyrrhizin, except for the steric configuration of the hydrogen atom located at the 18-position which is the α-configuration in the novel compound as contrasted with the β-configuration in the original compound.

In order to examine the toxicity of 18α-glycyrrhizins, a typical 18α-glycyrrhizin (i.e., 18α-glycyrrhizic acid monoammonium salt) was subjected to the following tests.

I. General Toxicity Test (1) Acute Toxicity Test

Ten female and ten male mice of the ICR strain (weighing 18–20 g and 23–25 g, respectively) were employed in this test. The 18α-glycyrrhizin was orally administered to each animal in a dose of 2.4 g/kg. As a result, none of the animals died. Moreover, no toxic symptoms were noted in all animals. (For details, see Draize, J. H. "Appraisal of the Safety of Chemicals in Foods, Drugs and Cosmetics", Associations of Food and Drug Officials of the United States.)

II. Specific Toxicity Tests (1) Temporary Skin Irritation Test

Six female rabbits of the New Zealand white strain (weighing 2.4–2.6 kg) were employed in this test. According to the closed patch test technique, 10%, 1% and 0.1% aqueous solutions of the 18α-glycyrrhizin were applied to the animals. When rated by Draize's method, the temporary irritation score was 0 at every concentration.

(2) Continuous Skin Irritation Test

Three female rabbits of the New Zealand white strain (weighing 2.7–2.9 kg) were employed. This test was performed over a period of 4 weeks, during which 25%, 2.5%, 0.25% and 0% aqueous solutions of the 18α-glycyrrhizin were continually applied to the dorsal skin (intact and injured skin areas) of the animals. The degree of irritation was rated by Draize's method. At each concentration, no abnormalities were noted in the intact and injured skin areas throughout the test period.

III. Human Patch Test

Eighteen male and five female healthy human subjects were employed in this test. According to the closed patch test technique, 10%, 1% and 0.1% aqueous solutions of the 18α-glycyrrhizin were applied to the subjects and the degree of irritation was examined after 24 hours. At each concentration, no abnormalities were noted in all cases.

Next, the glycyrrhizin compositions which can be used in the practice of the present invention are described in more detail.

These glycyrrhizin compositions can be prepared in the following manner: Any form of 18β-glycyrrhizin extracted from licorice root is dissolved in water or alcohol and heated in the presence of an alkali to convert from 30 to 98 mole % of the 18β-glycyrrhizin into an 18α-glycyrrhizic acid salt. Then, a glycyrrhizic acid composition can be obtained by isolating the resulting 18α-glycyrrhizic acid salt, together with the unconverted 18β-glycyrrhizin, from the reaction mixture in the form of free acid. Subsequently, the free acid thus obtained may be converted into a salt (a sodium, potassium or ammonium salt) as desired.

As stated before, the properties of 18α-glycyrrhizins are markedly different from those of 18β-glycyrrhizins. However, it has surprisingly been found that, just like 18α-glycyrrhizins in pure form, mixtures of an 18α-glycyrrhizin and an 18β-glycyrrhizin provide aqueous solutions which are stable even in an acidic pH range, so long as the mixtures have an 18α-glycyrrhizin content of not less than 30 mole % and preferably not less than 50 mole %. Moreover, these aqueous solutions do not undergo gelation even in an acidic pH range (i.e., in the pH range of from 2.0 to 6.0). Furthermore, such mixtures of an 18α-glycyrrhizin and an 18β-glycyrrhizin (i.e., the above-defined glycyrrhizin compositions) have beneficial properties which are substantially the same as those of pure 18α-glycyrrhizins. In addition, these glycyrrhizin compositions are advantageous in that they are less expensive and more economical than pure 18α-glycyrrhizins and require no viscosity modifiers in the preparation of clear liquid skin cosmetic compositions having high viscosity.

Table 3 comparatively shows some properties (i.e., solution viscosity, solution turbidity, dissolution time, and rate of foam disappearance in solution) of glycyrrhizin compositions (having various 18α-glycyrrhizin contents), pure 18α-glycyrrhizins and pure 18β-glycyrrhizins.

TABLE 3

| Sample Form | 18α-Isomer content (mole %) | Solution viscosity (cps) | Solution turbidity (ppm) | Dissolution time (sec) | Rate of foam disappearance in solution (%) |
|---|---|---|---|---|---|
| A | 0 | >30 | 59.5 | 660 | 29.0 |
| K | 0 | >30 | 87.1 | 490 | 28.7 |
| N | 0 | >30 | 87.0 | 480 | 28.8 |
| A | 30 | 2.01 | 0.5 | 60 | 29.1 |
| K | 30 | 2.05 | 0.6 | 32 | 29.2 |
| N | 30 | 2.05 | 0.6 | 32 | 29.3 |
| A | 50 | 1.08 | 0.3 | 60 | 89.4 |
| K | 50 | 1.09 | 0.3 | 30 | 89.5 |
| N | 50 | 1.09 | 0.3 | 30 | 89.5 |
| A | 70 | 1.06 | 0.3 | 58 | 89.6 |
| K | 70 | 1.05 | 0.4 | 30 | 89.7 |
| N | 70 | 1.05 | 0.4 | 30 | 89.8 |
| A | 80 | 1.09 | 0.3 | 57 | 90.1 |
| K | 80 | 1.08 | 0.4 | 30 | 90.2 |
| N | 80 | 1.08 | 0.4 | 30 | 90.3 |
| A | 98 | 1.07 | 0.3 | 55 | 90.7 |
| K | 98 | 1.07 | 0.3 | 31 | 90.8 |
| N | 98 | 1.07 | 0.3 | 31 | 90.8 |
| A | 100 | 1.06 | 0.2 | 53 | 90.8 |
| K | 100 | 1.07 | 0.3 | 32 | 91.0 |
| N | 100 | 1.07 | 0.3 | 32 | 91.1 |

Notes:
(1) Pure 18β-glycyrrhizins were used when the 18α-isomer content was 0%.
(2) Pure 18α-glycyrrhizins were used when the 18α-isomer content was 100%.
(3) A, N and K stand for monoammonium salt, monosodium salt and monopotassium salt, respectively.
(4) The solution viscosity was determined by adjusting an aqueous solution to pH 5.0 with 1N NaOH or 1N HCl and measuring its viscosity at 20° C. with an Ubbelohde viscometer.
(5) The solution turbidity was determined by subjecting an aqueous solution to direct turbidimetry.
(6) The dissolution time was determined by providing a sample powder having passed through an 80-mesh screen and measuring the time required to dissolve 0.5 g of the powder completely in 100 ml of water under definite stirring condition.
(7) The rate of foam disappearance in solution was determined by shaking a 0.5% aqueous solution and allowing it to stand for 90 minutes.

Thus, the above-defined 18α-glycyrrhizins and glycyrrhizin compositions have a number of beneficial properties which make it possible to prepare excellent skin cosmetic compositions readily and advantageously on an industrial scale. That is to say:

(1) The above-defined 18α-glycyrrhizins and glycyrrhizin compositions dissolve in water so rapidly that the time required to prepare the skin cosmetic composition of the present invention can be reduced significantly.
(2) The foam which is formed during the preparation of the skin cosmetic composition of the present invention can be destroyed simply by allowing it to stand for a relatively short period of time. Moreover, the time required to defoam the skin cosmetic composition of the present invention is short as compared with similar skin cosmetic compositions using conventional glycyrrhizins alone.
(3) The skin cosmetic composition of the present invention, which is prepared by using any of the above-defined 18α-glycyrrhizins and glycyrrhizin compositions as the solubilizing agent, shows a viscosity slightly higher than the above-described solution viscosity owing to the coexistence of various cosmetic base materials. However, the skin cosmetic composition of the present invention is not subject to viscosity build-up or gelation even if its pH value is in an acidic range (for example, in the range of from 4 to 6). According to the present invention, therefore, it is possible to provide acidic and clear liquid skin cosmetic compositions which could not be realized by the use of any conventional glycyrrhizin.

(4) In the skin cosmetic composition of the present invention, the 18α-glycyrrhizin or glycyrrhizin composition is completely dissolved to form a clear solution. Moreover, this skin cosmetic composition neither undergoes flocculation or sedimentation nor becomes turbid even after storage for a long period of time (at least 6 months) or freeze ($-10°$ C.) thaw ($30°$ C.) cycling. Thus, it can retain a clear and attractive appearance even under severe temperature conditions. (18β-Glycyrrhizins and certain types of synthetic surface-active agents induce a marked degree of sedimentation or turbidity under similar conditions.)

(5) The above-defined 18α-glycyrrhizins and glycyrrhizin compositions do not induce gelation in any desired pH range and can solubilize oily substances (for example, hormones, oil-soluble perfumes, oil-soluble colorants, oil-soluble vitamins and the like) in water stably and perfectly. Accordingly, the skin cosmetic composition of the present invention does not require the use of a solubilizing assistant such as alcohol or the like, in contrast to skin cosmetic compositions using conventional glycyrrhizins alone (for example, the hormone-blended lotion disclosed in Japanese Patent Laid-Open No. 151736/1977). Moreover, it can eliminate the necessity of adjusting its pH to 6.1 or greater (i.e., the necessity of adding a pH modifier thereto). Thus, in preparing the skin cosmetic composition of the present invention, its formulation can be designed with great ease.

(6) The above-defined 18α-glycyrrhizins and glycyrrhizin compositions are neither toxic nor irritative to the skin in contrast to synthetic surface-active agents, and have as excellent an antiphlogistic effect as coventional glycyrrhizins. It can be expected, therefore, that the skin cosmetic composition of the present invention has beneficial pharmacological effects on the skin.

(7) Owing to the presence of an 18α-glycyrrhizin or glycyrrhizin composition as defined above, not only moderate viscosity and good fluidity but also great affinity for the skin is imparted to the skin cosmetic composition of the present invention. Accordingly, in using this skin cosmetic composition, it can be easily taken out of the container and evenly spread over the skin surface to produce beneficial cosmetic effects. At the same time, the 18α-glycyrrhizin or glycyrrhizin composition present therein exerts a mild action on the skin and produces an antiphlogistic effect, thus giving a non-greasy, smooth and agreeable feeling.

The 18α-glycyrrhizins which are within the scope of the structural formula (1) given above and can be used in the practice of the present invention include 18α-glycyrrhizic acid monosodium salt, monopotassium salt, monoammonium salt, disodium salt, dipotassium salt and diammonium salt.

The 18β-glycyrrhizins (conventional glycyrrhizins) which are within the scope of the structural formula (2) given above include 18β-glycyrrhizic acid monoammonium salt, monopotassium salt, monosodium salt, disodium salt, dipotassium salt and diammonium salt.

In the skin cosmetic composition of the present invention, the above-enumerated 18α-glycyrrhizins may be used alone or in combination.

Where the solubilizing agent present in the skin cosmetic composition of the present invention comprises at least one 18α-glycyrrhizin, it is used in an amount of from 0.01 to 10% by weight and preferably from 0.1 to 3% by weight based on the total weight of the skin cosmetic composition. If the amount is less than 0.01% by weight, the oily substance cannot be solubilized satisfactorily, while it is greater than 10% by weight, the 18α-glycyrrhizin tends to become less soluble in this system.

In the glycyrrhizin compositions which consist of an 18α-glycyrrhizin within the scope of the structural formula (1) given above and an 18β-glycyrrhizin within the scope of the structural formula (2) given above and can be used in the practice of the present invention, both components desirably comprise a couple of compounds of the same type which are isomeric with each other, for example, 18α-glycyrrhizic acid monopotassium salt and 18β-glycyrrhizic acid monopotassium salt, or the like. More specifically, these glycyrrhizin compositions consist of from 30 to 98 mole % of the 18α-glycyrrhizin and from 2 to 70 mole % of the 18β-glycyrrhizin, and preferably consist of from 50 to 98 mole % of the 18α-glycyrrhizin and from 2 to 50 mole % of the 18β-glycyrrhizin.

Where the solubilizing agent present in the skin cosmetic composition of the present invention comprises such a glycyrrhizin composition, it is used in an amount of from 0.01 to 1% by weight and preferably from 0.1 to 3% by weight based on the total weight of the skin cosmetic composition. If the amount is less than 0.01% by weight, the oily substance cannot be solubilized satisfactorily, while it is greater than 10% by weight, the glycyrrhizin composition tends to become less soluble in this system.

The oily substances which can be used in the practice of the present invention include oil-soluble perfumes (for example, natural perfumes, synthetic perfumes and the like), oil-soluble hormones (for example, estradiol, ethynylestradiol, estrone, diethylstilbestrol, cortisone acetate and the like). These oily substances may be used alone or in combination. The amount of oily substance used in the skin cosmetic composition of the present invention is in the range of from 0.0001 to 1.0% by weight and preferably from 0.001 to 0.5% by weight based on the total weight of the skin cosmetic composition. If the amount is less than 0.0001% by weight, the characteristic effect of the oily substance is weakened, while if it is greater than 1.0% by weight, solubilization of the oily substance tends to become difficult.

The amount of water used in the skin cosmetic composition of the present invention is in the range of from 50 to 99% by weight and preferably from 60 to 99% by weight based on the total weight of the skin cosmetic composition.

Although the use of alcohol is not essential to the skin cosmetic composition of the present invention, an appropriate amount of alcohol may be incorporated thereinto so as to give a refreshing feeling to the skin and enhance the drying rate. In this case, the alcohol is used in an amount of at most 30% by weight and preferably from 5 to 20% by weight based on the total weight of the skin cosmetic composition.

Where the skin cosmetic composition of the present invention is adapted for use as a cleansing lotion, antiphlogistic lotion, hormone-blended lotion, acidic skin conditioning lotion, after-shave lotion or the like, it is unnecessary to incorporate a pigment thereinto. However, where the skin cosmetic composition of the present invention is adapted for use as a calamine lotion or liquid makeup base (under makeup clear lotion), it is recommended to incorporated a pigment thereinto in addition to the aforesaid ingredients. In this case, the pigment is used in an amount of at most 10% by weight and preferably from 0.5 to 7% by weight based on the total weight of the skin cosmetic composition. The pigments useful for this purpose include inorganic pigments such as titanium oxide, kaolin, yellow oxide of iron, red oxide of iron, black oxide of iron, talc and the like.

Furthermore, if desired, small amounts of cosmetically or pharmacologically effective substances, antiseptics, water-soluble colorants, water-soluble ultraviolet light absorbers and/or astringents may be added thereto.

The skin cosmetic composition of the present invention can be prepared by any well-known procedure. For example, an 18α-glycyrrhizin or a glycyrrhizin composition as defined above is dissolved in water. While the resulting aqueous solution is being stirred, a substance to be solubilized (i.e., an oily substance (as described above) or its alcoholic solution is added thereto and mixed therewith to obtain a clear liquid skin cosmetic composition. Alternatively, a substance to be solubilized (i.e., an oily substance as described above) is dispersed and dissolved in a concentrated aqueous solution of an 18α-glycyrrhizin or a glycyrrhizin composition as defined above. Then, the resulting solution is diluted with water to a predetermined volume.

The skin cosmetic compositions prepared in accordance with the present invention are adaptable for use as cleansing lotions, acidic skin conditioning lotions, astringent lotions, antiphlogistic lotions, after-shave lotions, calamine lotions, aqueous makeup bases and the like. These skin cosmetic compositions desirably have their pH values in an acidic range (preferably in the range of up to 6 and most preferably in the vicinity of the pH value (5.1) of the skin).

As stated before, the skin cosmetic compositions prepared in accordance with the present invention are so stable that they can be stored under severe conditions (for example, under severe temperature conditions) for a long period of time without undergoing gelation or sedimentation. Moreover, they retain a clear and attractive appearance and continue to have good fluidity and great affinity for the skin. Furthermore, when applied to the skin, they cause no irritation to the skin and give a non-greasy, smooth and agreeable feeling. Thus, these skin cosmetic composition have a very high commercial value.

The present invention is further illustrated by the following examples. In these examples, all parts and percentages are by weight.

EXAMPLE 1

(1) Preparation of 18α-Glycyrrhizic Acid Monoammonium Salt

Two hundred parts of 18β-glycyrrhizic acid monoammonium salt (having a purity of 80%) obtained from licorice root was dissolved in 1,000 parts of 4N NaOH and the resulting solution was heated under reflux for 8 hours at atmospheric pressure. Thereafter, the pH of the reaction mixture was adjusted to about 2 by the addition of sulfuric acid. The precipitate so formed was extracted with 500 parts of n-hexanol, and the resulting extract was alkalified with aqueous ammonia. After the n-hexanol was distilled off, the residue was recrystallized from 85% methanol to obtain 120 parts of mixed glycyrrhizic acid monoammonium salt (containing 73% of the 18α-isomer).

Then, the 18α-isomer contained therein was separated from the unconverted 18β-isomer in the following manner: A 1% aqueous solution of the aforesaid monoammonium salt was prepared, adjusted to pH 2.0 by the addition of hydrochloric acid, and then filtered through Toyo No. 3 filter paper. The precipitate collected on the filter paper was dissolved in dilute aqueous ammonia to form a 1% solution, which was again adjusted to pH 2.0 by the addition of hydrochloric acid and then filtered. After this procedure (which comprised acidifying the aqueous solution to form a precipitate and separating it by filtration) was repeated four times, the precipitate finally collected on the filter paper was dissolved in concentrated aqueous ammonia. To the resulting solution was added acetic acid (so as to give an acetic acid concentration of about 85%). The 18α-glycyrrhizic acid monoammonium salt which crystallized out of the solution was recrystallized from 80% acetic acid and then from 85% methanol, and further subjected to large-volume preparative high-speed liquid chromatography to remove any trace amounts of glycyrrhizin analogues. Thus, 18α-glycyrrhizic acid monoammonium salt was obtained in a pure form.

(2) Preparation of Cleansing Lotion

A. Formulation

| | | |
|---|---|---|
| 1 | 18α-Glycyrrhizic acid monoammonium salt | 1.0 part |
| 2 | Perfume (Lavender oil) | 0.03 part |
| 3 | FD & C Blue No. 1 (water-soluble dye) | 0.0001 part |
| 4 | Methyl p-hydroxybenzoate | 0.1 part |
| 5 | Purified water | 98.87 parts |

B. Procedure

The ingredient ① was mixed with and dissolved in part of the ingredient ⑤ to form an aqueous solution, in which the ingredient ② was dispersed and dissolved. On the other hand, the ingredients ③ and ④ were mixed with and dissolved in the remainder of the ingredient ⑤, and the resulting solution was homogeneously mixed with the previously prepared solution to obtain a cleansing lotion within the scope of the present invention. This cleansing lotion presented a light-blue and clear appearance, had a pH value of 4.3, and exhibited good fluidity characterized by a viscosity (at 20° C.) of 1.02 cps. After 6 months' storage in a thermostatic chamber at 5°–45° C., it remained clear and continued to present an attractive appearance. Moreover, no change in viscosity or pH was noted after this storage. This cleansing lotion could be easily applied to the skin to give a smooth finish and a non-greasy and agreeable feeling.

COMPARATIVE EXAMPLE 1

The procedure of Example 1 was repeated except that 18β-glycyrrhizic acid monoammonium salt was used in place of the 18α-glycyrrhizic acid monoammonium salt. The resulting lotion had a pH value of 4.3 and underwent gelation, so that it exhibited very poor fluidity, was hard to take out of the container, and could not be evenly applied to the skin.

EXAMPLE 2

(1) Preparation of 18α-Glycyrrhizic Acid Monopotassium Salt

The 18α-glycyrrhizic acid was dissolved in water, and the resulting solution was neutralized to pH 5.0 with potassium hydroxide. After the addition of acetic acid, the precipitated crystals were dried to obtain 18α-glycyrrhizic acid monopotassium salt in a pure form.

(2) Preparation of Cleansing Lotion

The procedure of Example 1 was repeated except that the 18α-glycyrrhizic acid monopotassium salt prepared as above was used in place of the 18α-glycyrrhizic acid monoammonium salt. The resulting cleansing lotion presented a light-blue and clear appearance, had a pH value of 4.2, and exhibited good fluidity characterized by a viscosity (at 20° C.) of 1.05 cps. After 6 months' storage in a thermostatic chamber at 5°–45° C., it remained clear and continued to present an attractive appearance. Moreover, no change in viscosity of pH was noted after this storage. This cleansing lotion could be easily applied to the skin to give a smooth finish and a non-greasy and agreeable feeling.

EXAMPLE 3

(1) Preparation of 18α-Glycyrrhizic Acid Monosodium Salt

Part of the 18α-glycyrrhizic acid was dissolved in water to form an aqueous solution, to which the stoichiometric amount of sodium carbonate was added. Then, this solution was evaporated to dryness to obtain 18α-glycyrrhizic acid monosodium salt.

(2) Preparation of Cleansing Lotion

The procedure of Example 1 was repeated except that the 18α-glycyrrhizic acid monosodium salt was used in place of the 18α-glycyrrhizic acid monoammonium salt. The resulting cleansing lotion exhibited as excellent properties (clarity, appearance, feeling, application properties, and storage stability) as the cleansing lotions of Examples 1 and 2 did. Immediately after preparation, this cleansing lotion had a viscosity (at 20° C.) of 1.05 cps and a pH value of 4.3. The viscosity remained unchanged after 6 months.

COMPARATIVE EXAMPLE 2

The procedure of Example 1 was repeated except that the monopotassium or monosodium salt of 18β-glycyrrhizic acid was used in place of the 18α-glycyrrhizic acid monoammonium salt. Similarly to the cleansing lotion of Comparative Example 1, each of the resulting cleansing lotions underwent gelation to exhibit very poor fluidity, was hard to take out of the container, and could not be evenly applied to the skin. The cleansing lotion prepared with the monosodium salt had a pH value of 4.3 and the cleansing lotion prepared with the monopotassium salt had a pH value of 4.2.

EXAMPLE 4

The procedure of Example 1 was repeated except that the disodium, dipotassium or diammonium salt of 18α-glycyrrhizic acid was used in place of the 18α-glycyrrhizic acid monoammonium salt. Each of the resulting cleansing lotions presented a light-blue and clear appearance, exhibited good fluidity, and could be easily applied to the skin to give a smooth finish and a non-greasy and agreeable feeling. Each of them had a viscosity of 1.06 cps, which remained unchanged after 6 months. Immediately after preparation, the cleansing lotions prepared with the dipotassium salt and the disodium salt had a pH value of 5.2 and the cleansing lotion prepared with the diammonium salt had a pH value of 4.6. These pH values remained unchanged after 6 months.

EXAMPLE 5

A number of acidic skin conditioning lotions were prepared according to the formulation given in Table 4. Some properties of the resulting acidic skin conditioning lotions are shown in Table 5.

TABLE 4

| Ingredient | Lotion No. 1** | No. 2* | No. 3* | No. 4* | No. 5** |
| --- | --- | --- | --- | --- | --- |
| Perfume [Ethylene Brassylate] (parts) | 0.00001 | 0.0001 | 0.01 | 1.0 | 2.0 |
| 18α-Glycyrrhizic acid monosodium salt (parts) | 5.0 | 5.0 | 5.0 | 5.0 | 5.0 |
| Colorant [D & C, Yellow No. 10] | 0.0001 | 0.0001 | 0.0001 | 0.0001 | 0.0001 |
| Methyl p-hydroxybenzoate | 0.05 | 0.05 | 0.05 | 0.05 | 0.05 |
| 1,3-Butylene glycol (parts) | 5.0 | 5.0 | 5.0 | 5.0 | 5.0 |
| Purified water (parts) | 89.95 | 89.95 | 89.94 | 89.0 | 88.0 |

TABLE 5

| Property | | Lotion No. 1** | No. 2* | No. 3* | No. 4* | No. 5** |
| --- | --- | --- | --- | --- | --- | --- |
| | pH | 4.5 | 4.5 | 4.2 | 4.0 | 4.0 |
| Clarity | Immediately after preparation | Good | Good | Very good | Good | Turbid |
| | After 6 months' storage at 5° C. | Good | Good | Very good | Good | Fairly turbid |
| Viscos- | Immediately | 1.02 | 1.02 | 1.02 | 1.08 | 1.13 |

TABLE 5-continued

| Property | | Lotion | | | | |
|---|---|---|---|---|---|---|
| | | No. 1** | No. 2* | No. 3* | No. 4* | No. 5** |
| ity | after preparation | | | | | |
| | After 6 months' storage at 5° C. | 1.13 | 1.13 | 1.13 | 1.14 | 1.35 |
| Fragrance | | Faint | Moderate | Moderate | Moderate | Too strong |
| Feeling | | Rather good | Good | Good | Good | Poor, greasy |

*These lotions are within the scope of the present invention.
**These lotions are outside the scope of the present invention and are listed for purposes of comparison.

It is evident from the data of Table 5 that if the amount of perfume used as an oily substance was less than 0.0001% by weight, the resulting lotion emits only faint fragrance, while if it is greater than 1.0% by weight, the resulting lotion emits too strong fragrance and becomes turbid.

EXAMPLE 6 (Acidic Skin Conditioning Lotions)

A number of acidic skin conditioning lotions were prepared according to the formulation given in Table 6. Some properties of the resulting acidic skin conditioning lotions are shown in Table 7.

TABLE 6

| Ingredient | Lotion | | | | | |
|---|---|---|---|---|---|---|
| | No. 1** | No. 2* | No. 3* | No. 4* | No. 5* | No. 6** |
| 18α-Glycyrrhizic acid monoammonium salt (parts) | 0.0001 | 0.01 | 0.1 | 3 | 10 | 15 |
| Perfume [bergamot oil] (parts) | 0.001 | 0.001 | 0.001 | 0.001 | 0.001 | 0.001 |
| Colorant [FD & C Blue No. 1] | 0.0001 | 0.0001 | 0.0001 | 0.0001 | 0.0001 | 0.0001 |
| Methyl p-hydroxybenzoate | 0.05 | 0.05 | 0.05 | 0.05 | 0.05 | 0.05 |
| Glycerol (parts) | 3.0 | 3.0 | 3.0 | 3.0 | 3.0 | 3.0 |
| Purified water (parts) | 96.5 | 96.94 | 96.85 | 93.95 | 86.95 | 81.95 |

TABLE 7

| Property | | Lotion | | | | | |
|---|---|---|---|---|---|---|---|
| | | No. 1** | No. 2* | No. 3* | No. 4* | No. 5* | No. 6** |
| | pH | 4.6 | 4.5 | 4.2 | 4.2 | 4.2 | 4.2 |
| Clarity | Immediately after preparation | Somewhat turbid | Clear | Very clear | Very clear | Clear | Turbid |
| | After 6 months' storage at 5° C. | Appearance of sediment | Clear | Very clear | Very clear | Clear | Deposition of crystals |
| Viscosity (cps, 20° C.) | | 1.00 | 1.00 | 1.02 | 1.03 | 2.3 | — |
| Feeling | | Non-greasy | Non-greasy, smooth | Non-greasy, smooth | Non-greasy, smooth | Non-greasy, smooth | Greasy |

*These lotions are within the scope of the present invention.
**These lotions are outside the scope of the present invention and are listed for purposes of comparison.

It is evident from the data of Table 7 that clear skin conditioning lotions having excellent properties are obtained when the 18α-glycyrrhizic acid monoammonium salt is used in an amount of from 0.1 to 10% by weight. If the amount is less than 0.01% by weight, turbidity and sediment appear, while if it is greater than 10% by weight, the 18α-glycyrrhizic acid monoammonium salt shows a slight reduction in solubility which results in the appearance of turbidity and the deposition of crystals and, moreover, the resulting lotion gives a disagreeable feeling when applied to the skin.

EXAMPLE 7 (Antiphlogistic Lotion)

A. Formulation

| | | |
|---|---|---|
| ① | 18α-Glycyrrhizic acid monopotassium salt | 0.4 part |
| ② | Propylene glycol | 5.0 parts |
| ③ | Estradiol | 0.001 part |
| ④ | Ethanol | 5.0 parts |
| ⑤ | Methyl p-hydroxybenzoate | 0.1 part |
| ⑥ | FD & C Blue No. 1 (water-soluble dye) | 0.0001 part |
| ⑦ | Purified water | 89.5 parts |

B. Procedure

The ingredients ①, ⑤ and ⑥ were mixed with and dissolved in the ingredient ⑦. On the other hand, the ingredients ②, ③ and ④ were mixed together, and this mixture was added to the previously prepared solution to obtain an antiphlogistic lotion within the scope of the present invention. This antiphlogistic lotion presented a light-blue and clear appearance, had a pH value of 4.2, and exhibited good fluidity characterized by a viscosity (at 20° C.) of 1.02 cps. After 6 months' storage in a thermostatic chamber at 5°–45° C., it remained clear. When applied to the skin, this antiphlogistic lotion gave a smooth finish and a refreshing, non-greasy and agreeable feeling. In addition, it had good moisture retention properties and caused a moist and pleasant sensation to the skin.

EXAMPLE 8 (After-shave lotion)

A. Formulation

| | | |
|---|---|---|
| ① | Ethanol | 30 parts |
| ② | Perfume (Clary sage oil) | 0.05 part |
| ③ | Isopropylmethylphenol | 0.01 part |
| ④ | Polyethylene glycol 200 | 2.0 parts |
| ⑤ | ε-Aminocaproic acid | 0.1 part |
| ⑥ | 18α-Glycyrrhizic acid disodium salt | 0.3 part |
| ⑦ | Yellow No. 203 (D & C, Yellow No. 10) | 0.0002 part |
| ⑧ | F.D. & C Blue No. 1 (water-soluble dye) | 0.0001 part |
| ⑨ | Water | 67.54 part |

B. Procedure

The ingredients ④, ⑤, ⑥, ⑦ and ⑧ were mixed with and dissolved in the ingredient ⑨. On the other hand, the ingredients ①, ② and ③ were mixed together, and this mixture was added to the previously prepared solution to obtain an after-shave lotion within the scope of the present invention. This after-shave lotion presented a light-yellow-green and clear appearance, had a pH value of 5.2, and exhibited good fluidity characterized by a viscosity (at 20° C.) of 1.04 cps. After 6 months' storage in a thermostatic chamber at 5°–45° C., it remained clear. When applied to the skin immediately after shaving, this after-shave lotion gave a smooth finish and a refreshing, non-sticky and agreeable feeling and, moreover, had the ability to alleviate itch and pain.

COMPARATIVE EXAMPLE 3

The procedure of Example 8 was repeated except that 18β-glycyrrhizic acid disodium salt was used in place of the 18α-glycyrrhizic acid disodium salt. The resulting after-shave lotion had a pH value of 4.3 and a viscosity of 2.12 cps. After 6 months' storage in a thermostatic chamber at 5°–45° C., the 18β-glycyrrhizic acid disodium salt produced insoluble matter (or sediment) which suspended or deposited in the after-shave lotion and imparted an undesirable appearance thereto.

EXAMPLE 9 (Calamine Lotion)

A. Formulation

| | | |
|---|---|---|
| ① | Ethyl alcohol | 5.0 parts |
| ② | 1,3-Butylene glycol | 3.0 parts |
| ③ | Sodium dihydrogen phosphate | 0.1 part |
| ④ | Titanium-oxide | 1.0 part |
| ⑤ | Zinc white | 0.5 part |
| ⑥ | Silicic anhydride | 0.5 part |
| ⑦ | Red oxide of iron | 0.01 part |
| ⑧ | 18α-Glycyrrhizic acid monoammonium salt | 0.4 part |
| ⑨ | Water | 89.39 parts |
| ⑩ | Perfume (Hiacinth absolute) | 0.1 part |

B. Procedure

The ingredients ②, ③ and ⑧ were mixed with and dissolved in the ingredient ⑨ to form an aqueous solution. On the other hand, the ingredients ④, ⑤, ⑥ and ⑦ were ground and mixed together, and this mixture was added to the previously prepared solution and uniformly dispersed therein by stirring. Then, the ingredient ⑩ dissolved in the ingredient ① was added to the resulting dispersion and intimately mixed therewith to obtain a calamine lotion within the scope of the present invention. This calamine lotion had a pH value of 5.4. When allowed to stand, it distinctly separated into a colorless, clear aqueous layer and a light-red pigment layer and thereby presented an attractive appearance. The time required for separation on standing was 15 minutes. After being allowed to stand for 2 hours, this calamine lotion exhibited very good miscibility by shaking. That is, a total of 5 shakes caused the two layers to be intimately mixed to form a system having the pigments uniformly dispersed therein. Moreover, these properties were highly reproducible even after 6 months. That is, the miscibility by shaking (a total of 5 shakes) and the time required for separation on standing (15 minutes) were equal to those observed immediately after preparation, and an attractive appearance showing distinctly separated two layers was produced repeatedly. When applied to the skin, this calamine lotion gave a smooth finish and a refreshing, non-greasy and agreeable feeling.

COMPARATIVE EXAMPLE 4

The procedure of Example 9 was repeated except that 0.4 part of 18β-glycyrrhizic acid monoammonium salt was used in place of the 18α-glycyrrhizic acid monoammonium salt. The resulting calamine lotion had a pH value of 5.4 and contained a partial gelation product which impaired the appearance of the pigment to a marked degree. Moreover, after being allowed to stand, it exhibited only poor miscibility by shaking. When this calamine lotion was applied to the skin, the partial gelation product made it impossible to give a smooth and stable finish and an agreeable feeling.

EXAMPLE 10 (Aqueous Makeup Base)

A. Formulation

| | | |
|---|---|---|
| ① | Ethyl alcohol | 5.0 parts |
| ② | Propylene glycol | 7.0 parts |
| ③ | Disodium hydrogen phosphate | 0.1 part |
| ④ | Alum | 0.07 part |
| ⑤ | Titanium oxide | 2.0 parts |
| ⑥ | Talc | 0.5 part |
| ⑦ | Yellow oxide of iron | 0.05 part |
| ⑧ | Red oxide of iron | 0.01 part |
| ⑨ | 18α-Glycyrrhizic acid monosodium salt | 1.0 part |
| ⑩ | Water | 84.17 parts |
| ⑪ | Perfume (Rose absolute) | 0.1 part |

B. Procedure

According to the above formulation, an aqueous makeup base within the scope of the present invention was prepared in the same manner as described in Example 9. When allowed to stand, this aqueous makeup base distinctly separated into a colorless, clear aqueous layer and a light-red pigment layer and thereby presented an attractive appearance, as was the case with the calamine lotion of Example 9. The time required for separation on standing was 17 minutes. After being allowed to stand for 2 hours, this aqueous makeup base exhibited very good miscibility by shaking. That is, a total of 5 shakes caused the two layers to be intimately mixed to form a system having the pigments uniformly dispersed therein. Moreover, these properties were highly reproducible even after 6 months. That is, the miscibility by shaking (a total of 5 shakes) and the time required for separation on standing (17 minutes) were equal to those observed immediately after preparation, and an attractive appearance showing distinctly separated two layers was produced repeatedly. When applied to the skin, this aqueous makeup base gave a smooth finish and a refreshing, non-greasy and agreeable feeling.

COMPARATIVE EXAMPLE 5

The procedure of Example 10 was repeated except that 18β-glycyrrhizic acid monosodium salt was used in place of the 18α-glycyrrhizic acid monosodium salt. The resulting aqueous makeup base soon separated into two layers and underwent complete gelation.

EXAMPLE 11

The procedure of Example 1 was repeated except that a glycyrrhizic acid monoammonium salt composition consisting of 69.6 mole % of the 18α-isomer and 30.4 mole % of the 18β-isomer was used in place of the 18α-glycyrrhizic acid monoammonium salt. The resulting cleansing lotion presented a light-blue and clear appearance, had a pH value of 4.3, and exhibited good fluidity characterized by a viscosity (at 20° C.) of 1.05 cps. After 6 months' storage in a thermostatic chamber at 5°–45° C., it remained clear and continued to present an attractive appearance. When applied to the skin, this cleansing lotion gave a smooth finish and a non-greasy and agreeable feeling.

EXAMPLE 12

The procedure of Example 7 was repeated except that a glycyrrhizic acid monopotassium salt composition consisting of 39.3 mole % of the 18α-isomer and 60.7 mole % of the 18α-isomer was used in place of the 18α-glycyrrhizic acid monopotassium salt. The resulting antiphlogistic lotion presented a light-blue and clear appearance, had a pH value of 4.2, and exhibited good fluidity characterized by a viscosity (at 20° C.) of 1.15 cps. After 6 months' storage in a thermostatic chamber at 5°–45° C., it remained clear. When applied to the skin, this antiphlogistic lotion gave a smooth finish and a refreshing, non-greasy and agreeable feeling. In addition, it had good moisture retention properties and caused a moist sensation to the skin.

EXAMPLE 13

A number of acidic skin conditioning lotions were prepared according to the formulation given in Table 8. Some properties of the resulting acidic skin conditioning lotions are shown in Table 9.

TABLE 8

| Ingredient | Lotion | | | | | |
|---|---|---|---|---|---|---|
| | No. 1** | No. 2* | No. 3* | No. 4* | No. 5* | No. 6** |
| Monosodium Glycyrrhizic composition [αβ =70 mole %:30 mole %] (parts) | 0.001 | 0.01 | 0.1 | 3.0 | 10 | 15 |
| Perfume (Bergamot oil) (parts) | 0.001 | 0.001 | 0.001 | 0.001 | 0.001 | 0.001 |
| Colorant [F. D & C. Blue No. 1] | 0.0001 | 0.0001 | 0.0001 | 0.0001 | 0.0001 | 0.0001 |
| Methyl p-hydroxybenzoate | 0.05 | 0.05 | 0.05 | 0.05 | 0.05 | 0.05 |
| Glycerol (parts) | 3.0 | 3.0 | 3.0 | 3.0 | 3.0 | 3.0 |
| Purified water (parts) | 96.95 | 96.94 | 96.85 | 93.95 | 86.95 | 81.95 |

TABLE 9

| Property | | Lotion | | | | | |
|---|---|---|---|---|---|---|---|
| | | No. 1** | No. 2* | No. 3* | No. 4* | No. 5* | No. 6** |
| | pH | 4.6 | 4.5 | 4.2 | 4.2 | 4.0 | 4.0 |
| Clarity | Immediately after preparation | Somewhat turbid | Clear | Very clear | Very clear | Clear | Turbid |
| | After 6 months' storage at 5° C. | Appearance of sediment | Clear | Very clear | Very clear | Clear | Deposition of crystals |
| Viscosity (cps, 20° C.) | | 1.00 | 1.00 | 1.02 | 1.06 | 2.46 | — |
| Feeling | | Non-greasy | Non-greasy, smooth | Non-greasy, smooth | Non-greasy, smooth | Non-greasy, smooth | Greasy |

*These lotions are within the scope of the present invention.
**These lotions are outside the scope of the present invention and are listed for purposes of comparison.

It is evident from the data of Table 9 that clear skin conditioning lotions having excellent properties are obtained when the monosodium glycyrrhizic composition is used in an amount of from 0.01 to 10% by weight. If the amount is less than 0.01% by weight, turbidity and sediment appear, while if it is greater than 10% by weight, the glycyrrhizic acid composition shows a slight reduction in solubility which results in the appearance of turbidity and the deposition of crystals and, moreover, the resulting lotion gives a disagreeable feeling when applied to the skin.

EXAMPLE 14

The procedure of Example 1 (2) was repeated except that the 18α- and 18β-glycyrrhizin and various glycyrrhizin compositions were used in place of the 18α-glycyrrhizic acid monoammonium salt. Some properties of the resulting cleansing lotion are shown in Table 10.

TABLE 10

| Sample | | | Viscosity of Products (cps) | Turbidity of Products (ppm) | Defoaming Rate of Products (%) |
|---|---|---|---|---|---|
| Form | 18α-Isomer content (mole %) | pH of* Products | | | |
| A | 0 | 5.1(4.3) | >30 | 60.5 | 22.3 |
| K | 0 | 5.0(4.2) | >30 | 88.8 | 25.5 |
| N | 0 | 5.0(4.3) | >30 | 87.5 | 21.4 |
| A | 30 | 5.0(4.2) | 2.00 | 0.7 | 35.2 |
| K | 30 | 5.0(4.3) | 2.10 | 0.6 | 37.1 |
| N | 30 | 5.1(4.3) | 1.97 | 0.8 | 30.7 |
| A | 50 | 4.9(4.3) | 1.07 | 0.3 | 88.8 |
| K | 50 | 5.0(4.3) | 1.08 | 0.4 | 89.7 |
| N | 50 | 5.0(4.3) | 1.09 | 0.5 | 89.8 |
| A | 70 | 5.0(4.3) | 1.06 | 0.4 | 91.3 |
| K | 70 | 5.0(4.2) | 1.05 | 0.4 | 90.5 |
| N | 70 | 5.0(4.2) | 1.05 | 0.5 | 90.7 |
| A | 80 | 5.0(4.3) | 1.08 | 0.4 | 91.2 |
| K | 80 | 5.0(4.3) | 1.09 | 0.4 | 91.4 |
| N | 80 | 5.0(4.3) | 1.09 | 0.4 | 90.4 |
| A | 98 | 4.9(4.3) | 1.06 | 0.4 | 91.2 |
| K | 98 | 5.0(4.3) | 1.07 | 0.4 | 90.8 |
| N | 98 | 5.0(4.3) | 1.06 | 0.5 | 90.8 |
| A | 100 | 5.0(4.3) | 1.04 | 0.3 | 92.2 |
| K | 100 | 5.0(4.2) | 1.07 | 0.4 | 91.6 |
| N | 100 | 5.0(4.3) | 1.06 | 0.4 | 90.1 |

*(1) The values of pH of products are those adjusted to about 5.0 with the 1N-NaOH solution.
(2) The values given in parentheses are those previous to the adjustment.
(3) A, N and K stand for monoammonium salt, monosodium salt and monopotassium salt, respectively.

EXAMPLE 15

A composition comprising 18α-glycyrrhizic acid monoammonium salt alone or a mixture having a specified ratio of 18α- and 18β-glycyrrhizic acid monoammonium salts according to the present invention was used as a solubilizing agent.

A number of cleansing lotions (skin conditioning lotions and so forth) were prepared by the process of the present invention according to the formulation given in Table II. Some properties of the resulting lotions are shown in Table 12.

TABLE 11

| Ingredient | Lotion | | | | | | | |
|---|---|---|---|---|---|---|---|---|
| | No. 1* | No. 2* | No. 3* | No. 4* | No. 5** | No. 6** | No. 7* | No. 8* |
| Glycyrrhizic acid monoammonium salt composition (parts) (18α/18β ratio) | 1.0 (98/2) | 1.0 (30/70) | 1.0 (98/2) | 1.0 (30/70) | 1.0 (20/80) | 1.0 (20/80) | 1.0 (100/0) | 1.0 (100/0) |
| Perfume (Lavender oil) (parts) | 0.03 | 0.03 | 0.03 | 0.03 | 0.03 | 0.03 | 0.03 | 0.03 |
| Ethanol (parts) | — | — | 10 | 10 | — | 10 | — | 10 |
| Methyl p-hydroxybenzoate (parts) | 0.1 | 0.1 | 0.1 | 0.1 | 0.1 | 0.1 | 0.1 | 0.1 |
| Purified water (parts) | 98.87 | 98.87 | 88.87 | 88.87 | 98.87 | 88.87 | 98.87 | 88.87 |

*These lotions are within the scope of the present invention.
**These lotions are outside the scope of the present invention and are listed for purposes of comparison.

TABLE 12

| | Property | Lotion | | | | | | | |
|---|---|---|---|---|---|---|---|---|---|
| | | No. 1* | No. 2* | No. 3* | No. 4* | No. 5** | No. 6** | No. 7* | No. 8* |
| | pH | 4.41 | 4.43 | 4.37 | 4.35 | 4.38 | 4.30 | 4.30 | 4.36 |
| Appearance | Permeability of light (%) | 88.0 | 82.0 | 97.0 | 94.5 | 78.5 | 90.5 | 88.0 | 97.0 |
| | Clarity (After 24 hours storage) | Clear | Clear | Clear | Clear | Nearly Clear | Clear | Clear | Clear |
| | Viscosity (cps at 20° C.) | 1.0 | 36.8 | 1.5 | 35.0 | 1,050 | 750 | 1.0 | 1.4 |
| | Fluidity | Good | Good | Good | Good | *1 Some gelation | *1 Some gelation | Good | Good |
| | Feeling | *2 Good | *2 Good | *2 Good | *2 Good | *3 A little poor | *3 A little poor | *2 Good | *2 Good |
| | *4 Appearance after 2 weeks and after 4 months storage at 5–45° C. | Good | Good | Good | Good | Good | Good (gelatinous) | Good | Good |

*1 Difficult to pour out of the vessel.
*2 Agreeable, neat and smooth feeling to the skin.
*3 Somewhat gelatinous and poor affinity to the skin, but smooth and agreeable finish upon application.
*4 No difference between the two periods.

COMPARATIVE EXAMPLE 6

In this example, a composition comprising 18β-glycyrrhizic acid monoammonium salt and a water-soluble polysaccharide disclosed in U.S. Pat. No. 4,278,657 as an emulsifying agent was used as a solubilizing agent according to the process of the present invention.

A number of cleansing lotions were prepared by the process of the present invention according to the formulation given in Table 13. Some properties of the resulting cleansing lotions are shown in Table 14.

Preparation of Cleansing Lotion

A. Preparation of Lotion Nos. 1–6

The ingredient ① was dissolved in a small amount of the ingredient ⑧, in which the ingredient ② is dispersed and dissolved. On the other hand, the ingredients ④ and ⑤ or ⑥ or ⑦ were mixed with and dissolved in a part of the ingredient ⑧ heated to 80° C., which was added to the previously prepared solution. To the resulting solution was added the remainder of the ingredient ⑧, which was homogeneously mixed to obtain a cleansing lotion.

B. Preparation of Lotion Nos. 7-9

In a solution obtained by dissolving the ingredient ① in a part of the ingredient ⑧ was mixed with a solution obtained by dissolving the ingredients ② and ④ in the ingredient ③. On the other hand, the ingredients ⑤ or ⑥ or ⑦ were mixed with and dissolved in a part of the ingredient ⑧ heated to 80° C., which was added to the previously prepared solution. To the resulting solution was added the remainder of the ingredient ⑧, which was homogeneously mixed to obtain a cleansing lotion.

good fluidity, agreeable feeling and good storage stability.

(2) In contrast thereto, the cleansing lotions in which an emulsifying agent comprising 18β-glycyrrhizic acid monoammonium salt and a water-soluble polysaccharide such as pectin, xanthan gum or locust bean gum according to U.S. Pat. No. 4,278,657 were used as a solubilizing agent according to the process of the present invention exhibited inferior properties such as turbid appearance despite the presence of ethanol, bad fluidity due to gelation, disagreeable feeling and poor storage stability.

TABLE 13

| | Ingredient | Lotion No. 1 | No. 2 | No. 3 | No. 4 | No. 5 | No. 6 | No. 7 | No. 8 | No. 9 |
|---|---|---|---|---|---|---|---|---|---|---|
| 1 | 18 β-Glycyrrhizic acid monoammonium salt (parts) | 1.0 | 1.0 | 1.0 | — | 1.0 | 1.0 | 1.0 | 1.0 | 1.0 |
| 2 | Perfume (Lavender oil) (parts) | 0.03 | 0.03 | 0.03 | 0.03 | 0.03 | 0.03 | 0.03 | 0.03 | 0.03 |
| 3 | Ethanol (parts) | — | — | — | — | — | — | 10 | 10 | 10 |
| 4 | Methyl p-hydroxybenzoate (parts) | 0.1 | 0.1 | 0.1 | 0.1 | 0.1 | 0.1 | 0.1 | 0.1 | 0.1 |
| 5 | Pectin (Degree of methyl esterification 70%) (parts) | — | 0.1 | 1.0 | 0.1 | — | — | — | 0.1 | 1.0 |
| 6 | Xanthan gum (parts) | — | — | — | — | 1.0 | — | — | — | — |
| 7 | Locust bean gum (parts) | — | — | — | — | — | 1.0 | — | — | — |
| 8 | Purified Water (parts) | 98.87 | 98.77 | 97.87 | 99.77 | 97.87 | 97.87 | 88.87 | 88.77 | 87.87 |

TABLE 14

| | Property | Lotion No. 1 | No. 2 | No. 3 | No. 4 | No. 5 | No. 6 | No. 7 | No. 8 | No. 9 |
|---|---|---|---|---|---|---|---|---|---|---|
| | pH | 4.50 | 4.47 | 4.28 | 4.03 | 4.53 | 4.55 | 4.37 | 4.37 | 4.18 |
| Appearance | Permeability of light (%) | 83.5 | 6.0 | 0.5 | 79.0 | 0 | 0 | 86.0 | 74.5 | 0 |
| | Clarity (After 24 hours storage) | Clear | Turbid | Turbid | Some turbidity | Turbid | Turbid | Clear | Nearly clear | Turbid |
| Viscosity (cps at 20° C.) | | 800 | 1,550 | 1,800 | 100 | 7,100 | 20,300 | 750 | 1,750 | 5,450 |
| | Fluidity | *1 | *1 | *1 | *2 | *1 | *1 | *1 | *1 | *1 |
| | | Gelation | Gelation | Gelation | Good | Gelation | Gelation | Gelation | Gelation | Gelation |
| | Feeling | *3 | *3 | *4 | *5 | *4 | *4 | *6 | *4 | *4 |
| | | A little poor | A little poor | A little poor | A little poor | A little poor | A little poor | A little poor | A little poor | A little poor |
| | *7 Appearance after 2 weeks and after 4 months storage at 5–45° C. | Good (gelatinous) | Separated into gel and water | Separated into gel and water | Perfume floats on lotion surface | Separated into gel and water | Separated into gel and water | Good (gelatinous) | Some deposition | Separated into gel and water |

*1 Difficult to pour out of the vessel.
*2 Easy to pour out of the vessel.
*3 Somewhat gelatinous and poor affinity to the skin, but smooth and agreeable finish upon application.
*4 Greasy and poor affinity to the skin upon application.
*5 Somewhat greasy upon application.
*6 Gelatinous and poor affinity to the skin.
*7 No difference between the two periods.

The following conclusions may be drawn from the results of Example 15 and Comparative Example 6.

(1) The cleansing lotions in which a composition comprising 18α-glycyrrhizic acid monoammonium salt alone or a mixture having a specified ratio of 18α- and 18β-glycyrrhizic acid monoammonium salts according to the present invention was used as a solubilizing agent, exhibited excellent properties such as clear appearance,

EXAMPLE 16

A number of cleansing lotions were prepared according to the formulation given in Table 15 by the process of the present invention using glycyrrhizic acid monopotassium salt in place of the glycyrrhizic acid monoammonium salt employed in Example 15 and Comparative Example 6. Some properties of the resulting cleansing lotions are shown in Table 16.

TABLE 15

| Ingredient | Lotion No. 1* | No. 2* | No. 3** | No. 4** | No. 5** | No. 6** | No. 7* |
|---|---|---|---|---|---|---|---|
| Glycyrrhizic acid monopotassium salt composition | 1.0 (80/20) | 1.0 (30/70) | 1.0 (0/100) | 1.0 (0/100) | 1.0 (0/100) | 1.0 (0/100) | 1.0 (100/0) |

TABLE 15-continued

| | Lotion | | | | | | |
|---|---|---|---|---|---|---|---|
| Ingredient | No. 1* | No. 2* | No. 3** | No. 4** | No. 5** | No. 6** | No. 7* |
| (parts) (18α/18β ratio) | | | | | | | |
| Perfume (Lavender oil) (parts) | 0.03 | 0.03 | 0.03 | 0.03 | 0.03 | 0.03 | 0.03 |
| Methyl p-hydroxybenzoate (parts) | 0.1 | 0.1 | 0.1 | 0.1 | 0.1 | 0.1 | 0.1 |
| Pectin (Degree of methyl esterification 70%) (parts) | — | — | — | 1.0 | — | — | — |
| Xanthan gum (parts) | — | — | — | — | 1.0 | — | — |
| Locust bean gum (parts) | — | — | — | — | — | 1.0 | — |
| Purified water (parts) | 98.87 | 98.87 | 98.87 | 97.87 | 97.87 | 97.87 | 98.87 |

*These lotions are within the scope of the present invention.
**These lotions are outside the scope of the present invention and are listed for purposes of comparison.

TABLE 16

| Property | | Lotion | | | | | | |
|---|---|---|---|---|---|---|---|---|
| | | No. 1* | No. 2* | No. 3** | No. 4** | No. 5** | No. 6** | No. 7* |
| | pH | 4.44 | 4.56 | 4.38 | 4.14 | 4.49 | 4.52 | 4.44 |
| Appearance | Permeability of light (%) | 94.0 | 92.0 | 74.0 | 0 | 0 | 0 | 94.1 |
| | Clarity (After 24 hours storage) | Clear | Clear | Nearly clear | Turbid | Turbid | Turbid | Clear |
| | Viscosity (cps at 20° C.) | 1 | 8 | 800 | 1,700 | 6,880 | 12,000 | 1 |
| | Fluidity | Good | Good | *1 Gelation | *1 Gelation | *2 Gelation | *2 Gelation | Good |
| | Feeling | *3 Good | *3 Good | *4 A little poor | *5 Poor | *5 Poor | *5 Poor | *3 Good |
| *6 Appearance after 2 weeks and after 4 months storage at 5-45° C. | | Good | Good | Good (gelatinous) | Separated into gel and water | Separated into gel and water | Separated into gel and water | Good |

*1 Difficult to pour out of the vessel.
*2 Impossible to pour out of the vessel.
*3 Agreeable, neat and smooth feeling to the skin.
*4 Gelatinous and poor affinity to the skin, but smooth and agreeable finish upon application.
*5 Greasy and poor affinity to the skin upon application.
*6 No difference between the two periods.

As is apparent from the above results, the functional effect of a combination of a glycyrrhizic acid monopotassium salt composition and a water-soluble polysaccharide disclosed in U.S. Pat. No. 4,278,657 is quite different from that of the present invention in which 18α-glycyrrhizic acid monoammonium salt alone or a mixture of 18α- and 18β-glycyrrhizic acid monoammonium salts is used characteristically as a solubilizing agent.

COMPARATIVE EXAMPLE 7

A number of cleansing lotions were prepared according to the formulation given in Table 17 and some properties of the resulting lotions having a pH value of from 9.0 to 9.4 are shown in Table 19.

Then, the pH value of the alkaline lotions of Table 19 were adjusted to 4.2 by adding citric acid as shown in Table 18.

Some properties of the lotions of Tables 17 and 18 are shown in Tables 19 and 20, respectively.

These formulations include 18α-glycyrrhetic acid potassium salt (or 18α-glycyrrhetinic acid potassium salt) as disclosed in Martindale, 26th Ed., 1972, the Extra Pharmacopoeia, pp. 563,714,715 and Beaton et al., Journal of the Chemical Society (London) 1955, Part 3, pp. 3126-3129 in place of 18α-glycyrrhizic acid potassium salt according to the present invention as the solubilizing agent.

TABLE 17

| | Lotion | | | | | | |
|---|---|---|---|---|---|---|---|
| Ingredient | No. 1 | No. 2 | No. 3 | No. 4 | No. 5 | No. 6 | No. 7 |
| 18α-Glycyrrhizic acid potassium salt (parts) | 0.1 | 0.2 | 0.3 | 0.4 | 0.6 | 0.8 | 1.0 |
| Perfume (Lavender oil) (parts) | 0.03 | 0.03 | 0.03 | 0.03 | 0.03 | 0.03 | 0.03 |
| Purified water (parts) | 99.87 | 99.77 | 99.67 | 99.57 | 99.37 | 99.17 | 98.97 |

TABLE 18

| | Lotion | | | | | | |
|---|---|---|---|---|---|---|---|
| Ingredient | No. 8 | No. 9 | No. 10 | No. 11 | No. 12 | No. 13 | No. 14 |
| 18α-Glycyrrhizic acid potassium salt (parts) | 0.1 | 0.2 | 0.3 | 0.4 | 0.6 | 0.8 | 1.0 |
| Perfume (Lavender oil) | 0.03 | 0.03 | 0.03 | 0.03 | 0.03 | 0.03 | 0.03 |

TABLE 18-continued

| Ingredient | Lotion | | | | | | |
|---|---|---|---|---|---|---|---|
| | No. 8 | No. 9 | No. 10 | No. 11 | No. 12 | No. 13 | No. 14 |
| (parts) | | | | | | | |
| Citric acid | Proper quantity | Proper quantity | Proper quantity | Proper quantity | Proper quantity | Proper quantity | Proper quantity |
| Purified water (parts) | 99.87 | 99.77 | 99.67 | 99.57 | 99.37 | 99.17 | 98.97 |

TABLE 19

| Property | | Lotion | | | | | | |
|---|---|---|---|---|---|---|---|---|
| | | No. 1 | No. 2 | No. 3 | No. 4 | No. 5 | No. 6 | No. 7 |
| | pH | 9.0 | 9.0 | 9.0 | 9.2 | 9.2 | 9.4 | 9.4 |
| Clarity (Visual method) | Immediately after preparation (RT)* | Turbid | Turbid | Turbid | Turbid | Turbid | Very turbid | Very turbid |
| | After 24 hours storage (RT)* | Turbid deposition | Turbid deposition | Turbid deposition | Very turbid deposition | Very turbid deposition | Very turbid deposition | Very turbid deposition |
| Viscosity (cps at 20° C.) | | 1.05 | 1.06 | 1.05 | 1.08 | 1.09 | 1.05 | 1.12 |
| Feeling (After 24 hours storage) | | Rough | Rough | Rough | Rough | Rough | Rough | Rough |

*Room Temperature

TABLE 20

| Property | | Lotion | | | | | | |
|---|---|---|---|---|---|---|---|---|
| | | No. 8 | No. 9 | No. 10 | No. 11 | No. 12 | No. 13 | No. 14 |
| | pH | 4.2 | 4.2 | 4.2 | 4.2 | 4.2 | 4.2 | 4.2 |
| Clarity (Visual method) | Immediately after preparation (RT)* | Very turbid deposition | Very turbid deposition | Very turbid deposition | Very turbid deposition | Most turbid deposition | Most turbid deposition | Most turbid deposition |
| | After 24 hours storage (RT)* | Very turbid deposition | Very turbid deposition | Very turbid deposition | Very turbid deposition | Most turbid deposition | Most turbid deposition | Most turbid deposition |
| Viscosity (cps at 20° C.) | | Impossible to measure due to too much deposition. | | | | | | |
| Feeling (After 24 hours storage) | | Rough | Rough | Rough | Rough | Rough | Rough | Rough |

*Room Temperature

COMPARATIVE EXAMPLE 8

A number of cleansing lotions were prepared in the same manner as in Comparative Example 7, except that an 18β-glycyrrhetic acid potassium salt was used in place of an 18α-glycyrrhetic acid potassium salt. Some properties of the resulting lotions are shown in Table 21.

Then, the pH value of these lotions was adjusted to 4.2 by adding citric acid in the same manner as in Comparative Example 7 and some properties thereof as shown in Table 22.

TABLE 21

| Property | | Lotion | | | | | | |
|---|---|---|---|---|---|---|---|---|
| | | No. 1 | No. 2 | No. 3 | No. 4 | No. 5 | No. 6 | No. 7 |
| | pH | 8.2 | 8.2 | 8.2 | 8.2 | 8.4 | 8.6 | 8.6 |
| Clarity (Visual method) | Immediately after preparation (RT)* | Turbid | Turbid | Turbid | Turbid | Somewhat turbid | Clear | Clear |
| | After 24 hours storage (RT)* | Turbid deposition | Turbid deposition | Turbid deposition | Turbid deposition | Turbid deposition | Turbid deposition | Turbid deposition |
| Viscosity (cps at 20° C.) | | 1.05 | 1.05 | 1.07 | 1.08 | 1.07 | 1.09 | 1.11 |
| Feeling (After 24 hours storage) | | Rough | Rough | Rough | Rough | Rough | Rough | Rough |

*Room Temperature

TABLE 22

| Property | | Lotion | | | | | | |
|---|---|---|---|---|---|---|---|---|
| | | No. 8 | No. 9 | No. 10 | No. 11 | No. 12 | No. 13 | No. 14 |
| | pH | 4.2 | 4.2 | 4.2 | 4.2 | 4.2 | 4.2 | 4.2 |
| Clarity (Visual method) | Immediately after preparation (RT)* | Very turbid deposition | Very turbid deposition | Very turbid deposition | Very turbid deposition | Most turbid deposition | Most turbid deposition | Most turbid deposition |
| | After 24 hours storage (RT)* | Very turbid deposition | Very turbid deposition | Very turbid deposition | Very turbid deposition | Most turbid deposition | Most turbid deposition | Most turbid deposition |
| Viscosity (cps at 20° C.) | | Impossible to measure due to too much deposition | | | | | | |
| Feeling | | Rough | Rough | Rough | Rough | Rough | Rough | Rough |

TABLE 22-continued

| Property | Lotion | | | | | | |
|---|---|---|---|---|---|---|---|
| | No. 8 | No. 9 | No. 10 | No. 11 | No. 12 | No. 13 | No. 14 |
| (After 24 hours storage) | | | | | | | |

*Room Temperature

The following conclusion may be drawn from the results of Comparative Examples 7 and 8.

(1) The lotion having an alkaline pH value, e.g. from 8.2 to 9.4 is formed when an 18α-glycyrrhetic acid potassium salt or an 18β-glycyrrhetic acid potassium salt is used as a solubilizing agent.
(2) Such a lotion is of no practical use, since it is inferior in clarity and feeling.
(3) Even if the pH value of the above lotion is adjusted to acidic, e.g. 4.2, a large quantity of deposition material is formed and it is impossible to obtain a clear skin conditioning lotion having an excellent clarity and an agreeable feeling which is a feature of the present invention.

What is claimed is:

1. A clear, liquid skin cleansing and conditioning cosmetic composition which consists essentially of
  (a) a solubilizing agent selected from the group consisting of from 0.01 to 10% by weight based on the total weight of the skin cosmetic composition of at least one 18α-glycyrrhizin of the structural formula:

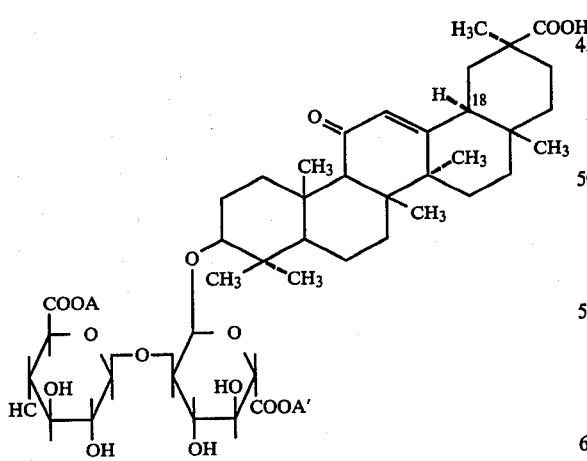

in which A and A' independently represent sodium atoms, potassium atoms or ammonium groups, and from 0.01 to 10% by weight based on the total weight of the skin cosmetic composition of a glycyrrhizin composition consisting essentially of from 30 to 98 mole % of said 18α-glycyrrhizin and from 2 to 70 mole % of an 18β-glycyrrhizin of the structural formula:

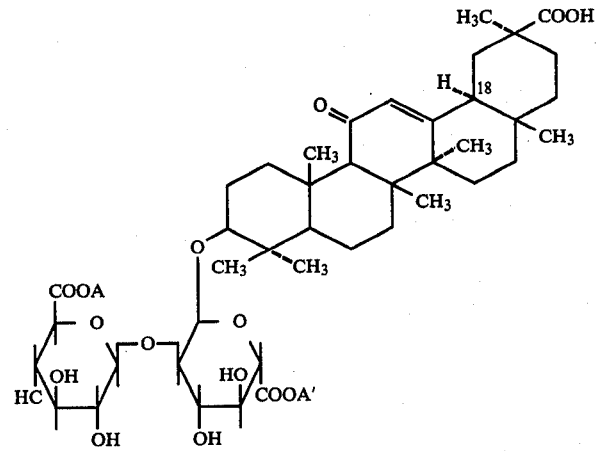

in which A and A' independently represent sodium atoms, potassium atoms or ammonium groups;
  (b) an oily substance selected from the group consisting of oil soluble natural and synthetic perfumes, in an amount of from 0.0001 to 1.0% by weight based on the total weight of the skin cosmetic composition; and
  (c) water in an amount of from 50 to 99% by weight based on the total weight of the skin cosmetic composition;
said skin cosmetic composition having a pH value in the range of from 4.2 to 6.4.

2. The skin cosmetic composition of claim 1 wherein the glycyrrhizin composition consists of from 50 to 98 mole % of the 18α-glycyrrhizin and from 2 to 50 mole % of the 18β-glycyrrhizin.

3. The skin cosmetic composition of claim 1 wherein said 18α-glycyrrhizin is present in an amount of from 0.1 to 3% by weight based on the total weight of the skin cosmetic composition.

4. The skin cosmetic composition of claim 1 wherein the glycyrrhizin composition is present in an amount of from 0.1 to 3.0% by weight based on the total weight of the skin cosmetic composition.

5. The skin cosmetic composition of claim 1 wherein the water is present in an amount of from 50 to 99% by weight based on the total weight of the skin cosmetic composition.

6. The skin cosmetic composition of claim 1 which further includes alcohol in an amount of at most 30% by weight based on the total weight of the skin cosmetic composition.

7. The skin cosmetic composition of claim 1 which further includes a pigment in an amount of at most 10% by weight based on the total weight of the skin cosmetic composition.

8. The skin cosmetic composition of claim 7 wherein the pigment is at least one inorganic pigment selected from the group consisting of titanium dioxide, kaolin, yellow oxide or iron, red oxide of iron, black oxide or iron, and talc.

9. The skin cosmetic composition of claim 1, 6 or 7 which has a pH value in the range of from 4.2 to 6.0.

10. The skin cosmetic composition of claim 1, 6 or 7 which has a pH value in the range of from 4.8 to 5.4.

* * * * *